United States Patent [19]

Surrey

[11] 3,940,441
[45] Feb. 24, 1976

[54] N,N'-BISPHENOXYBENZYL-BRIDGED-DIAMIDES

[75] Inventor: Alexander R. Surrey, Albany, N.Y.

[73] Assignee: Sterling Drug Inc., New York, N.Y.

[22] Filed: July 15, 1974

[21] Appl. No.: 488,330

Related U.S. Application Data

[60] Division of Ser. No. 331,325, Feb. 9, 1973, Pat. No. 3,876,701, which is a division of Ser. No. 29,643, April 17, 1970, Pat. No. 3,772,370, which is a continuation-in-part of Ser. No. 652,013, July 10, 1967, abandoned, which is a continuation of Ser. No. 390,451, Aug. 18, 1964, abandoned.

[52] U.S. Cl...... 260/562 B; 260/553 A; 260/562 A; 260/562 P
[51] Int. Cl.² ...................................... C07C 103/34
[58] Field of Search......... 260/562 B, 562 A, 562 P, 260/553 A

[56] References Cited
UNITED STATES PATENTS 3,553,260   1/1971   Felder ............................ 260/562 A
3,798,276   3/1974   Bayer et al. ..................... 260/562 A Primary Examiner—C. Davis
Attorney, Agent, or Firm—Robert K. Bair; Theodore C. Miller; B. Woodrow Wyatt

[57] ABSTRACT

Alkylenediamine derivatives substituted on each nitrogen atom by 4-(4'-nitrophenoxy)benzyl or 4-(4'-aminophenoxy)benzyl, optionally substituted additionally on each nitrogen by lower-alkyl, phenylcarbamyl or dihaloacetyl and optionally interrupted in alkylene by cycloalkylene, phenylene, alkylated-phenylene, pyridylene, furylene and thiazolylene. The compounds, which have antibacterial activity, are prepared stepwise by reacting an alkylenediamine with two molar equivalents of 4-(4'-nitrophenoxy)benzaldehyde and reducing the resulting bis(benzal)alkanediamines.

5 Claims, No Drawings

N,N'-BISPHENOXYBENZYL-BRIDGED-DIAMIDES

This application is a division of my copending application Ser. No. 331,325, filed Feb. 9, 1973, now U.S. Pat. No. 3,876,701 which is in turn a division of my copending application Ser. No. 29,643, filed Apr. 17, 1970, now U.S. Pat. No. 3,772,370, which is in turn a continuation-in-part of my copending application Ser. No. 652,013, filed July 10, 1967 and now abandoned, which is in turn a continuation of my copending application Ser. No. 390,451, filed Aug. 18, 1964 and now abandoned.

This invention relates to alkanediamine derivatives.

The invention resides in the concept of an alkanediamine substituted on each nitrogen by 4-(4'-nitrophenoxy)-benzyl or 4-(4'-aminophenoxy)benzyl and optionally substituted additionally on each nitrogen by lower-alkyl, phenylcarbamyl or dihaloacetyl.

Illustrative and preferred embodiments of my compounds are those of Formula I

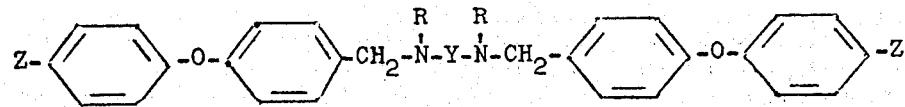

I where Z is nitro or amino, R is hydrogen, lower-alkyl, phenylcarbamyl or dihaloacetyl, and Y is alkylene having from two to ten carbon atoms and having its connecting linkages on different carbon atoms. The alkylene moiety can be interrupted by O, S, NH, N(lower-alkyl), cycloalkylene having from three to six ring carbon atoms, phenylene, phenylene having from one to four lower-alkyl substituents, pyridylene, furylene and thiazolylene.

The term "lower-alkyl," as used herein, e.g., for R in Formula I, means lower-alkyl radicals having preferably from one to six carbon atoms which can be arranged as straight or branched chains, and are illustrated by methyl, ethyl, n-propyl, isopropyl, 2-butyl, n-hexyl, and the like.

The term "dihaloacetyl," as used herein, e.g., for R in Formula I, means acetyl radicals disubstituted by any halogen which can be the same or different for a given radical, and are illustrated by dichloroacetyl, difluoroacetyl, dibromoacetyl, diiodoacetyl, bromochloroacetyl, chlorofluoroacetyl, and the like.

As used in Formula I and elsewhere herein the alkylene radical Y when uninterrupted has from two to ten carbon atoms and has its connecting linkages on different carbon atoms, as illustrated by —CH$_2$CH$_2$—, —CH(CH$_3$)CH$_2$—,

—CH$_2$CHCH$_3$,

—C(CH$_3$)$_2$CH$_2$—, —CH$_2$CH$_2$CH$_2$—,

—CH$_2$CHCH$_2$CH$_3$,

—CH$_2$CH$_2$CH$_2$CH$_2$—,

—(CH$_2$)$_5$—, —(CH$_2$)$_6$—, —(CH$_2$)$_7$—, —(CH$_2$)$_8$—, and the like; and, when interrupted, is illustrated by —CH$_2$CH$_2$OCH$_2$CH$_2$—, —CH$_2$CH$_2$OCH$_2$CH$_2$CH$_2$—, —CH$_2$CH$_2$SCH$_2$CH$_2$—, —CH$_2$CH$_2$CH$_2$SCH$_2$CH$_2$CH$_2$—, —CH$_2$CH$_2$NHCH$_2$CH$_2$—, —CH$_2$CH$_2$CH$_2$NHCH$_2$CH$_2$CH$_2$—, —CH$_2$CH(CH$_3$)NHCH(CH$_3$)CH$_2$—, —CH(CH$_3$)CH$_2$NHCH$_2$CH(CH$_3$)—, —CH(CH$_3$)CH$_2$NHCH(CH$_3$)CH$_2$, —CH$_2$CH$_2$CH$_2$N(CH$_3$)CH$_2$CH$_2$CH$_2$—,

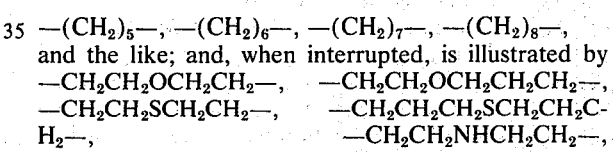

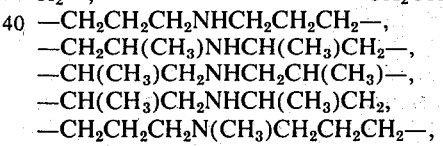

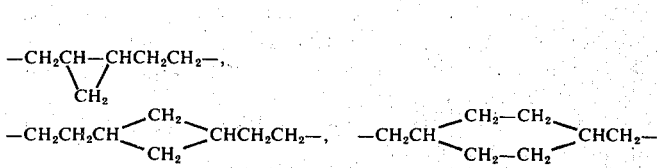

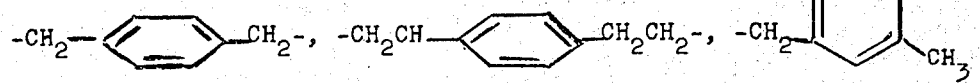

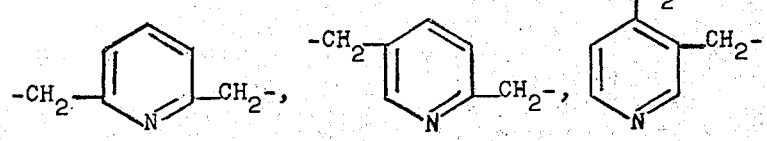

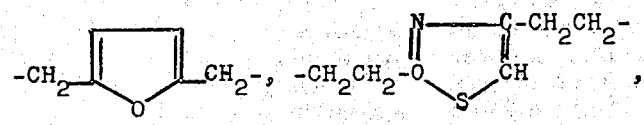

and the like. The two connecting linkages of each interrupting cycloalkylene, phenylene, pyridylene, furylene and thiazolylene moiety can be attached to any pair of available carbon atoms of said ring moiety.

The compounds of Formula I where R is hydrogen and Z is nitro (Formula IA) are prepared as follows:

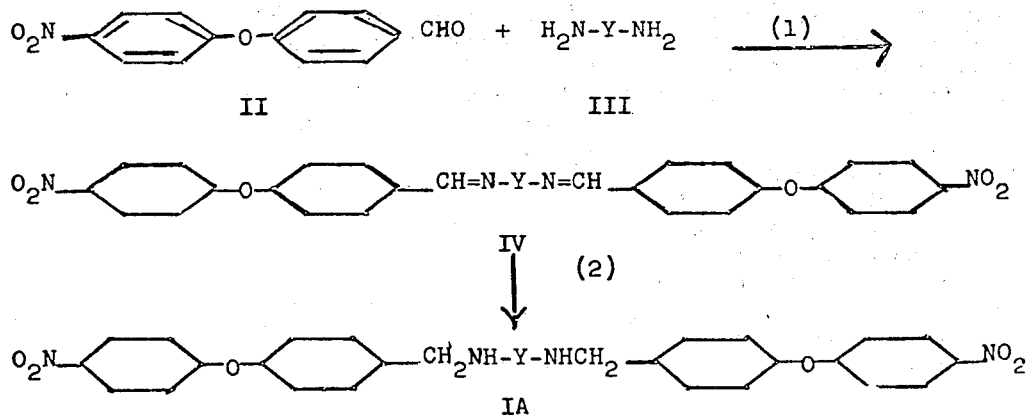

The intermediate N,N'-bis[4-(4'-nitrophenoxy)benzal]alkanediamines of Formula IV also constitute another aspect of my invention; these compounds are not only useful as intermediates in the preparation of the compounds of Formula IA but also have antibacterial activity as noted hereinbelow. The intermediate diamines of Formula III are generally known compounds which are prepared by generally known methods, e.g., by the reductive amination of the corresponding bisoxoalkyl compound, the amination of the bis-haloalkyl compound or the reduction of the bis-nitrile, bis-oxime, bis-azide, or analogous other bis-higher-valency nitrogen compound. The diamine intermediates in some cases are also conveniently prepared from unsymmetrical starting materials as will be apparent to those skilled in the art of organic chemistry.

The compounds of Formula I where Z is $NO_2$ and R is lower-alkyl, phenylcarbamyl or dihaloacetyl are prepared from the compounds of Formula IA by reacting a compound of Formula IA with an alkylating agent, phenylisocyanate or a dihaloacetyl halide respectively.

The compounds of Formula I where Z is $NH_2$ are prepared by reducing the corresponding compounds where Z is $NO_2$ utilizing reducing agents effective to reduce nitro to amino.

The above-noted processes are illustrated in the specific examples hereinbelow.

My compounds of Formula I where Z is amino are useful in the free base from or in the form of their acid-addition salts, and both forms are within the purview of the invention, and, in fact, are considered to be one and the same invention. The acid-addition salts are simply a more convenient form for use; and, in practice, use of the salt form inherently amounts to use of the base form. The acids which can be used to prepare the acid-addition salts are preferably those which produce, when combined with the free base, chemotherapeutically acceptable salts, that is, salts whose anions are relatively innocuous to the animal organism in chemotherapeutic doses of the salts, so that the beneficial properties inherent in the free base are not vitiated by side effects ascribable to the anions; in other words, the latter do not substantially affect the chemotherapeutic properties inherent in the cations. In practicing my invention, I found it convenient to employ the hydrochloride salt. However, other appropriate chemotherapeutically acceptable salts within the scope of the invention are those derived from mineral acids such as hydrobromic acid, hydriodic acid, nitric acid, phosphoric acid, sulfamic acid, and sulfuric acid; and organic acids such as acetic acid, citric acid, tartaric acid, lactic acid, methanesulfonic acid, ethanesulfonic acid, quinic acid, and the like, giving the hydrobromide, hydriodide, nitrate, phosphate, sulfamate, sulfate, acetate, citrate, tartrate, lactate, methanesulfonate, ethanesulfonate and quinate, respectively.

The acid-addition salts are prepared preferably by reacting the free base and acid in an organic solvent, e.g., ethanol, in which case the salt separates directly or can be obtained by concentration of the solution.

Although chemotherapeutically acceptable salts are preferred, all acid-addition salts are within the scope of my invention. All acid-addition salts are useful as sources of the free base form even if the particular salt per se is not desired as the final product, as for example when the salt is formed for purposes of purification or identification, or when it is used as an intermediate in preparing a chemotherapeutically acceptable salt by ion exchange procedures.

The molecular structures of the compounds of my invention are established by their modes of synthesis and corroborated by the correspondence of calculated and found values for the elementary analyses.

My compounds of Formulas I and IV have been tested by standard biological evaluation procedures and found to have antibacterial properties, e.g., when tested according to standard in vitro bacteriological evaluation procedures. They have been found to possess antibacterial activity, for example, against *Staphylococcus aureus*, *Eberthella typhi*, *Clostridium welchii*, and *Pseudomonas aeruginosa*, at test concentration levels in the range of about 0.005 mg./cc. to about 1.0 mg./cc., as illustrated below in the examples.

Also, some of my compounds of Formula IV have been tested by standard chemotherapeutic evaluation procedures in vivo in hamsters and found to possess amebacidal activity. As illustrated below in the examples, these compounds when administered orally to hamsters infected with *Endamoeba criceti* have been found to clear the animals of the amebic infection at dose levels from about 12.5 to 300 mg./kg./day.

The following examples will further illustrate the invention without, however, limiting it thereto.

EXAMPLE 1

A. N,N'-bis[4-(4'-nitrophenoxy)benzal]-1,6-hexanediamine — A solution containing 48.7 g. of 4-(4'-nitrophenoxy)benzaldehyde and 11.6 g. of 1,6-hexanediamine in 250 cc. of benzene was refluxed with a continuous separator connected to the reaction vessel for removal of water formed by the reaction. Although the reaction was complete within two hours, as shown by the theoretical quantity of water in the separator, the mixture was allowed to reflux overnight. The reaction mixture was concentrated and the crystalline product that separated was collected. It was recrystallized from chloroform to yield the product, N,N'-bis[4-(4'-nitrophenoxy)benzal]-1,6-hexanediamine, m.p. 141.8°–143.0°C. (corr.).

Anal. Calcd. for $C_{32}H_{30}N_4O_6$: C, 67.83; H, 5.34; N, 9.89. Found: C, 67.49; H, 5.33; N, 9.71.

N,N'-bis[4-(4'-nitrophenoxy)benzal]-1,6-hexanediamine when administered orally to hamsters infected with *Endamoeba criceti* was found to clear 4 out of 10, 6 out of 10, and 3 out of 5 of the animals at respective dose levels of 25, 50 and 100 mg./kg./day. When tested by standard in vitro bacteriological evaluation procedures, N,N'-bis-[4-(4'-nitrophenoxy)benzal]-1,6-hexanediamine was found to have bacteriostatic activity against *Staphylococcus aureus, Eberthella typhi, Clostridium welchii* and *Pseudomonas aeruginosa* at respective concentrations of 0.1, 1.0, 0.5 and 1.0 mg./cc.

Following the procedure described in Example 1A using molar equivalent quantities of 4-(4'-nitrophenoxy)-benzaldehyde and the appropriate diamine, the following compounds can be prepared:

B.  N,N'-bis[4-(4'-nitrophenoxy)benzal]-1,4-butanediamine, using 1,4-butanediamine.

C.  N,N'-bis[4-(4'-nitrophenoxy)benzal]-1,10-decanediamine, using 1,10-decanediamine.

D.  Bis{2-[4-(4'-nitrophenoxy)benzalamino]ethyl}ether, using bis(2-aminoethyl) ether.

E.  Bis{2-[4-(4'-nitrophenoxy)benzalamino]ethyl} sulfide, using bis(2-aminoethyl) sulfide.

EXAMPLE 2

N,N'-bis[4-(4'-nitrophenoxy)benzal]-1,8-octanediamine was prepared following the procedure described in Example 1A using 48.7 g. of 4-(4'-nitrophenoxy)-benzaldehyde, 14.4 g. of 1,8-octanediamine, and 250 cc. of benzene. There was thus obtained a quantitative yield of the product, N,N'-bis[4-(4'-nitrophenoxy)benzal]-1,8-octanediamine. After recrystallization once from chloroform-n-pentane and once from isopropyl alcohol, it melted at 101.2°–103.0°C. (corr.).

Anal. Calcd. for $C_{34}H_{34}N_4O_6$: C, 68.68; H, 5.76; N, 9.42. Found: C, 68.91; H, 5.87; N, 9.53.

N,N'-bis[4-(4'-nitrophenoxy)benzal]-1,8-octanediamine when administered orally to hamsters infected with *Endamoeba criceti* was found to clear 1 out of 5, 2 out of 5, and 2 out of 5 of the animals at respective dose levels of 12.5, 25 and 50 mg./kg./day. When tested by standard in vitro bacteriological evaluation procedures, N,N'-bis[4-(4'-nitrophenoxy)benzal]-1,8-octanediamine was found to have bacteriostatic activity against *Staphylococcus aureus, Eberthella typhi* and *Clostridium welchii* at respective concentrations of 0.1, 1.0 and 0.75 mg./cc.

EXAMPLE 3

N,N'-bis[4-(4'-nitrophenoxy)benzal]-1,2-ethanediamine was prepared as in Example 1A using 40.3 g. of 4-(4'-nitrophenoxy)benzaldehyde, 4.98 g. of ethylenediamine, 200 cc. of benzene, and a reflux period of ninety minutes. The product was recrystallized from dioxane to yield 28.5 g. of the product, N,N'-bis[4-(4'-nitrophenoxy)-benzal]-1,2-ethanediamine, m.p. 167.2°–169.4°C. (corr.).

Anal. Calcd. for $C_{28}H_{22}N_4O_6$: C, 65.87; H, 4.35; N, 10.97. Found: C, 65.96; H, 4.27; N, 10.72.

N,N'-bis[4-(4'-nitrophenoxy)benzal]-1,2-ethanediamine when administered orally to hamsters infected with *Endamoeba criceti* was found to clear 2 out of 5 of the animals at a dose level of 100 mg./kg./day.

EXAMPLE 4

N,N'-bis[4-(4'-nitrophenoxy)benzal]-1,3-propanediamine was prepared as in Example 1A using 48.6 g. of 4-(4'-nitrophenoxy)benzaldehyde, 7.4 g. of 1,3-propanediamine, 200 cc. of benzene, and a reflux period of 3 hours. After several recrystallizations from acetonitrile, there was obtained 10.1 g. of N,N'-bis[4-(4'-nitrophenoxy)-benzal]-1,3-propanediamine, m.p. 119.4°–121.6°C. (corr.).

Anal. Calcd. for $C_{29}H_{24}N_4O_6$: C, 66.40; H, 4.61; N, 10.68. Found: C, 66.71; H, 4.51; N, 10.69.

EXAMPLE 5

A.  Trans-N,N'-bis[4-(4'-nitrophenoxy)benzalaminomethyl]-1,4-cyclohexane was prepared as in Example 1A using 24.3 g. of 4-(4'-nitrophenoxy)benzaldehyde, 7.1 g. of trans-1,4-bis(aminomethyl)cyclohexane, 100 cc. of benzene, and a reflux period of one hour. There was thus obtained 2.4 g. of trans-N,N'-bis[4-(4'-nitrophenoxy)benzalaminomethyl]-1,4-cyclohexane, m.p. 196.6°–206.0°C. (corr.) after recrystallization from dioxane.

Anal. Calcd. for $C_{34}H_{32}N_4O_6$: C, 68.91; H, 5.45; N, 9.46. Found: C, 68.65; H, 5.41; N, 9.60.

When tested by standard in vitro bacteriological evaluation procedures, trans-N,N'-bis[4-(4'-nitrophenoxy)-benzalaminomethyl]-1,4-cyclohexane was found to have bacteriostatic activity against *Staphylococcus aureus, Eberthella typhi* and *Clostridium welchii* at respective concentrations of 0.1, 0.1 and 0.075 mg./cc.

B.  N,N'-bis[4-(4'-nitrophenoxy)benzalaminomethyl]-1,2-cyclobutane is prepared following the procedure described in Example 5A using corresponding molar equivalent quantities of 4-(4'-nitrophenoxy)benzaldehyde and 1,2-bis(aminomethyl)cyclobutane.

EXAMPLE 6

A.  N,N'-bis[4-(4'-nitrophenoxy)benzyl]-1,8-octanediamine — To a filtered mixture containing 65.8 g. of N,N'-bis[4-(4'-nitrophenoxy)benzal]-1,8-octanediamine, 1000 cc. of methanol, and 150 cc. of dioxane was added in small portions 12.6 g. of sodium borohydride. The mixture was stirred for an additional 90 minutes after all of the sodium borohydride had been added. The mixture was then concentrated to remove the solvents and the concentrate added to 750 cc. of water. The resulting precipitate was collected, recrystallized from cyclohexane, washed with water and dried to yield 51.5 g. of the product, N,N'-bis[4-(4'-nitrophenoxy)benzyl]-1,8-octanediamine, m.p. 59.6°–61.0°C. (corr.).

Anal. Calcd. for $C_{34}H_{38}N_4O_6$: C, 68.20; H, 6.40; N, 9.36. Found: C, 68.47; H, 6.15; N, 9.12.

N,N'-bis[4-(4'-nitrophenoxy)benzyl]-1,8-octanediamine when tested according to standard in vitro bacteriological procedures was found to have antibacterial activity, for example, as follows:

| | Minimum Effective Concentration (mg./cc.) | |
| --- | --- | --- |
| | Bacteriostatic | Bactericidal |
| *Staphylococcus aureus* | 0.0005 | 0.005 |
| *Eberthella typhi* | 0.0075 | 0.025 |
| *Clostridium welchii* | 0.05 | 0.075 |
| *Pseudomonas aeruginosa* | 0.75 | 1.0 |

Following the procedure described in Example 6A using molar equivalent quantities of the appropriate N,N'-bis[4-(4'-nitrophenoxy)benzal]-diamine and sodium borohydride, the following compounds can be prepared.

B. N,N'-bis[4-(4'-nitrophenoxy)benzyl]-1,3-propanediamine, using N,N'-bis[4-(4'-nitrophenoxy)-benzal]-1,3-propanediamine.

C. N,N'-bis[4-(4'-nitrophenoxy)benzyl]-1,4-butanediamine, using N,N'-bis[4-(4'-nitrophenoxy)-benzal]-1,4-butanediamine.

D. N,N'-bis[4-(4'-nitrophenoxy)benzyl]-1,10-decanediamine, using N,N'-bis[4-(4'-nitrophenoxy)-benzal]-1,10-decanediamine.

E. Bis{2-[4-(4'-nitrophenoxy)benzylamino]ethyl} ether, using bis{2-[4-(4'-nitrophenoxy)benzalamino]ethyl} ether.

F. Bis{2-[4-(4'-nitrophenoxy)benzylamino]ethyl} sulfide, using bis{2-[4-(4'-nitrophenoxy)benzalamino]ethyl} sulfide.

EXAMPLE 7

N,N'-bis[4-(4'-nitrophenoxy)benzyl]-1,6-hexanediamine was prepared following the procedure described in Example 6A using 63.5 g. of N,N'-bis[4-(4'-nitrophenoxy)-benzal]-1,6-hexanediamine, 1000 cc. of methanol, 150 cc. of dioxane, 12.6 g. of sodium borohydride. There was thus obtained 48.5 g. of N,N'-bis[4-(4'-nitrophenoxy)benzyl]-1,6-hexanediamine, m.p. 89.0°–91.2°C. (corr.).

Anal. Calcd. for $C_{32}H_{34}N_4O_6$: C, 67.34; H, 6.00; N, 9.82. Found: C, 67.64; H, 5.79; N, 9.64.

N,N'-bis[4-(4'-nitrophenoxy)benzyl]-1,6-hexanediamine when tested according to standard in vitro bacteriological procedures was found to have antibacterial activity, for example, as follows:

| | Minimum Effective Concentration (mg./cc.) | |
|---|---|---|
| | Bacteriostatic | Bactericidal |
| Staphylococcus aureus | 0.001 | 0.0075 |
| Eberthella typhi | 0.0075 | 0.05 |
| Clostridium welchii | 0.025 | 0.025 |
| Pseudomonas aeruginosa | 0.25 | 0.5 |

EXAMPLE 8

N,N'-bis[4-(4'-nitrophenoxy)benzyl]-1,2-ethanediamine. To a stirred mixture containing 18.5 g. of N,N'-bis[4-(4'-nitrophenoxy)benzal]-1,2-ethanediamine, 500 cc. of methanol, and 200 cc. of dioxane was added in portions over a period of about fifteen minutes 4.2 g. of sodium borohydride. The mixture was then stirred for an additional 2 hours, allowed to stand overnight, concentrated in vacuo to remove the solvents and treated with water. The oily layer was extracted with benzene, the benzene solution dried over anhydrous sodium sulfate and the benzene distilled off to yield an oil which crystallized on standing. The crystalline material was washed with carbon tetrachloride and recrystallized twice from propionitrile. There was thus obtained 4.1 g. of N,N'-bis[4-(4'-nitrophenoxy)-benzyl]-1,2-ethanediamine, m.p. 119.2°–124.8°C. (corr.).

Anal. Calcd. for $C_{28}H_{26}N_4O_6$: C, 65.36; H, 5.09; N, 10.89. Found: C, 65,35; H, 5.13; N, 11.05.

N,N'-bis[4-(4'-nitrophenoxy)benzyl]-1,2-ethanediamine when tested according to standard in vitro bacteriological procedures was found to have antibacterial activity, for example, as follows:

| | Minimum Effective Concentration (mg./cc.) | |
|---|---|---|
| | Bacteriostatic | Bactericidal |
| Staphylococcus aureus | 0.01 | 0.05 |
| Eberthella typhi | 0.075 | >0.1 |
| Clostridium welchii | 0.0005 | 0.001 |
| Pseudomonas aeruginosa | 0.075 | >0.1 |

EXAMPLE 9A 2,2'-Dimethylbis{2-[4-(4'-nitrophenoxy)benzylamino]-ethyl}amine and 1,2'-Dimethylbis{2-[4-(4'-nitrophenoxy)benzylamino]ethyl}amine (Mixture of Isomers) — To a stirred solution containing 29 g. of 2,2'-dimethylbis{2-[4-(4'-nitrophenoxy)benzalamino]ethyl}amine and 1,2'-dimethylbis{2-[4(4'-nitrophenoxy)benzalamino]ethyl}amine (mixture of isomers) in 500 cc. of methanol was added in portions 5.7 g. of sodium borohydride and the resulting mixture was stirred for 2 hours. The reaction mixture was concentrated, water was added, the aqueous mixture was made basic with 35 percent aqueous sodium hydroxide solution, and the basic mixture was extracted with tetrahydrofuran. The extracted mixture was concentrated to a semisolid, benzene was added and distilled off, and the remaining solid was taken up in ether. The ether solution was filtered, the filtrate concentrated to yield a semi-solid which was dissolved in ethanol. To the ethanol solution was added 15 cc. of concentrated hydrochloric acid and the mixture concentrated in vacuo to yield a semi-solid which crystallized on standing. The solid was recrystallized from methanol to yield 6.9 g. of 2,2'-dimethylbis{2-[4-(4'-nitrophenoxy)benzylamino]-ethyl}amine and 1,2'-dimethylbis{2-[4-(4'-nitrophenoxy)benzylamino]ethyl}amine (approximately 3:1 mixture of isomers) trihydrochloride mixture, m.p. 236.0°–241.2°C. (corr.).

Anal. Calcd. for $C_{32}H_{35}N_5O_6 \cdot 3HCl$: C, 15.30; N, 10.08. Found: C, 15.28; N, 9.91.

2,2'-Dimethylbis{2-[4-(4'-nitrophenoxy)benzylamino]ethyl}amine and 1,2'-dimethylbis{2-[4-(4'-nitrophenoxy)benzylamino]ethyl}-amine trihydrochloride mixture, when tested according to standard in vitro bacteriological procedures, was found to have antibacterial activity, for example, as follows:

| | Minimum Effective Concentration (mg./cc.) | |
|---|---|---|
| | Bacteriostatic | Bactericidal |
| Staphylococcus aureus | 0.005 | 0.025 |
| Eberthella typhi | 0.1 | 0.25 |
| Clostridium welchii | 0.001 | 0.005 |
| Pseudomonas aeruginosa | 0.5 | >1.0 |
| Streptococcus sp. | 0.0075 | 0.01 |

The above intermediate, 2,2'-dimethylbis{2-[4-(4'-nitrophenoxy)benzalamino]ethyl}amine and 1,2'-dimethylbis{2-[4-(4'-nitrophenoxy)benzalamino]ethyl}amine (mixture of isomers) was prepared following the procedure described in Example 1 using 24.3 g. of 4-(4'-nitrophenoxy)benzaldehyde, 6.55 g. of 2,2'-dimethylbis(2-aminoethyl)amine and 1,2'-dimethylbis(2-aminoethyl)amine (mixture of isomers), 100 cc. of benzene and a reflux period of 5 hours. The reaction mixture was concentrated in vacuo to yield 29.0 g. of 2,2'-dimethylbis{2-[4-(4'-nitrophenoxy)benzalamino]ethyl}amine and 1,2'-dimethylbis-{2-[4-(4'- nitrophenoxy)benzalamino]ethyl} amine (mixture of isomers).

EXAMPLE 9B

Bis{3-[4-(4'-nitrophenoxy)benzylamino]propyl}amine. To a stirred mixture of 80.0 g. of bis{3-[4-(4'-nitrophenoxy)-benzalamino]propyl}amine and 1 l. of methanol was added in portions 13 g. of sodium borohydride. The mixture was stirred for 2 hours while the temperature was maintained at 8°–10°C., then concentrated. A solution of the residue in benzene was washed with sodium hydroxide solution, dried over potassium carbonate and concentrated. Treatment of a solution of the residue in isopropyl alcohol with an excess of concentrated hydrochloric acid afforded a precipitate, which, when washed with ether and recrystallized from water, gave bis{3-[4-(4'-nitrophenoxy)benzylamino]propyl}amine trihydrochloride, m.p. 278°C. (decomposition, uncorr.).

Anal. Calcd. for $C_{32}H_{35}N_5O_6 \cdot 3HCl$: Cl, 15.30. Found: Cl, 15.08.

Bis{3-[4-(4'-nitrophenoxy)benzylamino]propyl}amine trihydrochloride, when tested according to standard in vitro bacteriological procedures, was found to have antibacterial activity, for example, as follows:

| Minimum Inhibitory Concentration(meg./ml.) | |
|---|---|
| Staphylococcus aureus | 0.05 |
| Pseudomonas aeruginosa | 3.1 |
| Escherichia coli | 0.2 |
| Proteus vulgaris | 125 |

The above intermediate, bis{3-[4-(4'-nitrophenoxy)benzalamino]propyl}amine, was prepared following the procedure described in Example 1 using 55.5 g. of 4-(4'-nitrophenoxy)-benzaldehyde, 15 g. of bis(3-aminopropyl)amine, 500 cc. of benzene and a reflux period of 2 hours. The reaction mixture was concentrated in vacuo to yield 80 g. of bis{3-[4-(4'-nitrophenoxy)benzalamino]propyl}amine.

EXAMPLE 10

A. Trans-1,4-bis[4-(4'-nitrophenoxy)benzylaminomethyl]cyclohexane — A mixture containing 15.2 g. of trans-N,N'-bis[4-(4'-nitrophenoxy)benzalaminomethyl]-1,4-cyclohexane, 2.94 g. of sodium borohydride, and 300 cc. of ethanol was stirred for three hours and allowed to stand overnight. The reaction mixture was filtered and the filtrate distilled to remove the solvent. The remaining solid was suspended in a mixture of 300 cc. of dioxane and 500 cc. of methanol, 3 g. of sodium borohydride added, and the mixture stirred for four hours. The resulting solution was concentrated in vacuo to yield a solid which was washed with water, collected, dried in vacuo, and recrystallized from benzene-n-hexane to yield 11.2 g. of the product, trans-1,4-bis[4-(4'-nitrophenoxy)-benzylaminomethyl]cyclohexane, m.p. 127.6°–130.8°C. (corr.).

Anal. Calcd. for $C_{34}H_{36}N_4O_6$: C, 68.43; H, 6.08; N, 9.39. Found: C, 68.77; H, 5.91; N, 9.46.

Trans-1,4-bis[4-(4'-nitrophenoxy)benzylaminomethyl]-cyclohexane when tested according to standard in vitro bacteriological procedures was found to have antibacterial activity, for example, as follows:

| | Minimum Effective Concentration (mg./cc.) | |
|---|---|---|
| | Bacteriostatic | Bactericidal |
| Staphylococcus aureus | 0.01 | 0.05 |
| Eberthella typhi | 0.05 | 0.075 |
| Clostridium welchii | 0.1 | 0.1 |
| Streptococcus sp. | 0.025 | 0.025 |

B. 1,2-bis[4-(4'-nitrophenoxy)benzylaminomethyl]-cyclobutane can be prepared following the procedure described in Example 10A using corresponding molar equivalent quantities of 1,2-bis[4-(4'-nitrophenoxy)-benzalaminomethyl]cyclobutane and sodium borohydride.

EXAMPLE 11

A. N,N'-Dimethyl-N,N'-bis[4-(4'-nitrophenoxy)-benzyl]-1,6-hexanediamine — To a solution containing 19 g. of N,N'-bis[4-(4'-nitrophenoxy)benzyl]-1,6-hexanediamine in 69 g. of formic acid was added 53.3 g. of 37 percent aqueous formaldehyde solution, and the resulting reaction mixture was refluxed on a steam bath for 12 hours. The reaction mixture was concentrated in vacuo to yield a semi-solid which was taken up in methanol; the methanol solution made basic with 35 percent aqueous sodium hydroxide solution; the alkaline solution diluted with water to a volume of 250 cc. and extracted with tetrahydrofuran. The extract was concentrated in vacuo to yield an oil, the oil was treated with ether and the mixture filtered to remove insoluble material. The ether solution was concentrated in vacuo to yield an oil which crystallized on cooling. The solid was dissolved in 50 cc. of isopropyl alcohol; 5 cc. of concentrated hydrochloric acid was added; and the mixture was concentrated in vacuo to yield a solid. The solid was first recrystallized by dissolving in 50 cc. of methanol, filtering the solution and diluting the filtrate with about 250 cc. of ethyl acetate; and then it was recrystallized a second time from dimethylformamide to yield 11.4 g. of N,N'-dimethyl-N,N'-bis[4-(4'-nitrophenoxy)benzyl]-1,6-hexanediamine as its dihydrochloride, m.p. 231.4°–233.2°C. (corr.).

Anal. Calcd. for $C_{34}H_{38}N_4O_6 \cdot 2HCl$: C, 60.80; H, 6.00; Cl, 10.56. Found: C, 60.51; H, 5.83; Cl, 10.46.

N,N'-Dimethyl-N,N'-bis[4-(4'-nitrophenoxy)benzyl]-1,6-hexanediamine when tested according to standard in vitro bacteriological procedures was found to have antibacterial activity, for example, as follows:

| | Minimum Effective Concentration (mg./cc.) | |
|---|---|---|
| | Bacteriostatic | Bactericidal |
| Staphylococcus aureus | 0.005 | 0.25 |
| Eberthella typhi | 0.5 | 0.75 |
| Clostridium welchii | 0.25 | 0.5 |
| Streptococcus sp. | 0.005 | 0.005 |

Following the procedure described in Example 11A using molar equivalent quantities of the appropriate N,N'-bis[4-(4'-nitrophenoxy)benzyl]-diamine and alkylating agent, the following compounds can be obtained:

B. Bis{2-[4-(4'-nitrophenoxy)benzylmethylamino]-ethyl} ether, using bis{2-[4-(4'-nitrophenoxy)benzylamino]-ethyl} ether and a mixture of formic acid and formaldehyde.

C. Bis{2-[4-(4'-nitrophenoxy)benzylmethylaminol]-ethyl} sulfide, using bis{2-[4-(4'-nitrophenoxy)benzylamino]-ethyl} sulfide and a mixture of formic acid and formaldehyde.

D. Bis{3-[4-(4'-nitrophenoxy)benzylmethylamino)-propyl} methylamine, using bis{3-[4-(4'-nitrophenoxy)benzylamino]propyl} amine and a mixture of at least three molar equivalents of each of formic acid and formaldehyde per mole of the amine.

E. Trans-1,4-bis[4-(4'-nitrophenoxy)benzylmethylaminomethyl]cyclohexane, using trans-1,4-bis[4-

(4'-nitrophenoxy)benzylamino]cyclohexane and a mixture of formic acid and formaldehyde.

F. N,N'-diethyl-N,N'-bis[4-(4'-nitrophenoxy)-benzyl]-1,8-octanediamine, using N,N'-bis[4-(4'-nitrophenoxy) benzyl]-1,8-hexanediamine and ethyl iodide as the alkyline agent, preferably in the presence of an acid-acceptor, e.g., sodium carbonate, and using an aqueous ethanol reaction medium.

G. N,N'-di-n-butyl-N,N'-bis[4-(4'-nitrophenoxy)-benzyl]-1,6-hexanediamine, using N,N'-bis[4-(4'-nitrophenoxy)-benzyl]-1,6-hexanediamine and n-butyl bromide, preferably using sodium carbonate as an acid-acceptor and aqueous ethanol as the reaction medium.

H. N,N'-di-n-hexyl-N,N'-bis[4-(4'-nitrophenoxy)-benzyl]-1,4-butanediamine, using N,N'-bis[4-(4'-nitrophenoxy)benzyl]-1,4-butanediamine and n-hexyl iodide, preferably in an aqueous ethanol reaction mixture in the presence of sodium carbonate.

EXAMPLE 12

A. N,N'-bis[4-(4'-nitrophenoxy)benzyl]-N,N'-bis(-phenylcarbamyl)-1,6-hexanediamine - 5.7 g. of N,N'-bis[4-(4'-nitrophenoxy)benzyl]-1,6-hexanediamine was dissolved by warming with 25 cc. of benzene, and to this solution was added 2.62 g. of phenyl isocyanate, whereupon there separated an oily product which crystallized on standing. The solid was collected and recrystallized from tetrahydrofuran-ethyl acetate to yield 4.8 g. of N,N'-bis[4-(4'-nitrophenoxy)benzyl]-N,N'-bis(-phenylcarbamyl)-1,6-hexanediamine, m.p. 179.8°–180.2°C. (corr.).

Anal. Calcd. for $C_{46}H_{44}N_6O_8$: C, 68.36; H, 5.49; N, 10.40. Found: C, 68.33; H, 5.63; N, 10.35.

N,N'-bis[4-(4'-nitrophenoxy)benzyl]-N,N'-bis-(phenylcarbamyl)-1,6-hexanediamine when tested according to standard in vitro bacteriological procedures was found to have antibacterial activity, for example, as follows:

|  | Minimum Effective Concentration (mg./cc.) | |
|---|---|---|
|  | Bacteriostatic | Bactericidal |
| Staphylococcus aureus | 0.075 | 0.075 |
| Eberthella typhi | 0.075 | >0.1 |
| Clostridium welchii | 0.075 | 0.1 |
| Pseudomonas aeruginosa | 0.075 | >0.1 |

Following the procedure described in Example 12A using molar equivalent quantities of the appropriate N,N'-bis[4-(4'-nitrophenoxy)benzyl]-diamine and phenyl isocyanate, the following compounds can be prepared:

B. N,N'-bis[4-(4'-nitrophenoxy)benzyl]-N,N'-bis(-phenylcarbamyl)-1,8-octanediamine, using N,N'-bis[4-(4'-nitrophenoxy)benzyl]-1,8-octanediamine.

C. N,N'-bis[4-(4'-nitrophenoxy)benzyl]-N,N'-bis(-phenylcarbamyl)-1,3-propanediamine, using N,N'-bis[4-(4'-nitrophenoxy)benzyl]-1,3-propanediamine.

EXAMPLE 13

A. N,N'-bis(dichloroacetyl)-N,N'-bis[4-(4'-nitrophenoxy)benzyl]-1,2-ethanediamine — To a solution containing 11.4 g. of N,N'-bis[4-(4'-nitrophenoxy)benzyl]-1,2-ethanediamine in 100 cc. of ethylene dichloride cooled to 5°C. was added slowly with stirring a solution of 7.4 g. of dichloroacetyl chloride in 25 cc. of ethylene dichloride. The reaction mixture was kept basic by slow addition of 10 percent aqueous sodium hydroxide solution and was stirred for one additional hour at room temperature. The layers were separated, and the ethylene dichloride layer was washed successively with dilute aqueous hydrochloric acid and water, and then concentrated in vacuo to remove the solvent. The remaining material crystallized on standing and was recrystallized from ethyl acetate to yield 3.2 g. of N,N'-bis(dichloroacetyl)-N,N'-bis[4-(4'-nitrophenoxy)benzyl]-1,2-ethanediamine, m.p. 150.6°–152.6°C. (corr.).

Anal. Calcd. for $C_{32}H_{26}Cl_4N_4O_8$: C, 52.20; H, 3.56; Cl, 19.26. Found: C, 52.44; H, 3.60; Cl, 19.07.

N,N'-bis(dichloroacetyl)-N,N'-bis[4-(4'-nitrophenoxy)benzyl]-1,2-ethanediamine when tested according to standard in vitro bacteriological procedures was found to have antibacterial activity, for example, as follows:

|  | Minimum Effective Concentration (mg./cc.) | |
|---|---|---|
|  | Bacteriostatic | Bactericidal |
| Staphylococcus aureus | 0.75 | >1.0 |
| Eberthella typhi | 0.75 | 0.75 |
| Clostridium welchii | 0.75 | >1.0 |
| Pseudomonas aeruginosa | 0.75 | 0.75 |

Following the procedure described in Example 13A using corresponding molar equivalent quantities of N,N'-bis-[4-(4'-nitrophenoxy)benzyl]-diamine and dihaloacetyl halide, the following compounds can be prepared:

B. N,N'-bis(dichloroacetyl)-N,N'-bis[4-(4'-nitrophenoxy)benzyl]-1,6-hexanediamine, using N,N'-bis[4-(4'-nitrophenoxy)benzyl]-1,6-hexanediamine and dichloroacetyl chloride.

C. N,N'-bis(dichloroacetyl)-N,N'-bis[4-(4'-nitrophenoxy)benzyl]-1,8-octanediamine, using N,N'-bis[4-(4'-nitrophenoxy)benzyl]-1,8-octanediamine and dichloroacetyl chloride.

D. N,N'-bis(dibromoacetyl)-N,N'-bis[4-(4'-nitrophenoxy)benzyl]-1,6-hexanediamine, using N,N'-bis[4-(4'-nitrophenoxy)benzyl]-1,6-hexanediamine and dibromoacetyl chloride.

E. N,N'-bis(bromochloroacetyl)-N,N'-bis[4-(4'-nitrophenoxy)benzyl]-1,8-octanediamine, using N,N'-bis[4-(4'-nitrophenoxy)benzyl]-1,8-octanediamine and bromochloroacetyl chloride.

F. N,N'-bis(diiodoacetyl)-N,N'-bis[4-(4'-nitrophenoxy)benzyl]-1,6-hexanediamine, using N,N'-bis[4-(4'-nitrophenoxy)benzyl]-1,6-hexanediamine and diiodoacetyl chloride.

G. N,N'-bis(difluoroacetyl)-N,N'-bis[4-(4'-nitrophenoxy)benzyl]-1,8-octanediamine, using N,N'-bis[4-(4'-nitrophenoxy)benzyl]-1,8-octanediamine and difuloroacetyl chloride.

H. N,N'-bis(dichloroacetyl)-trans-1,4-bis[4-(4'-nitrophenoxy)benzylaminomethyl]cyclohexane, using trans-1,4-bis[4-(4'-nitrophenoxy)benzylaminomethyl]cyclohexane and dichloroacetyl chloride.

I. N,N'-bis(dichloroacetyl)-1,4-bis[4-(4'-nitrophenoxy)benzylaminomethyl]benzene, using 1,4-bis[4-(4'-nitrophenoxy)benzylaminomethyl]benzene and dichloroacetyl chloride.

EXAMPLE 14

A. N,N'-bis[4-(4'-aminophenoxy)benzyl]-1,8-octanediamine — To a stirred suspension of 6.0 g. of N,N'-bis[4-(4'-nitrophenoxy)benzyl]-1,8-octanediamine in 50 cc. of methanol was added 1.9 g. of sodium borohydride and 100 mg. of 10 percent palladium-oncharcoal. The reaction mixture was stirred for 10 minutes, allowed to stand an additional 15 minutes, and then filtered to remove the catalyst. The filtrate was distilled to remove the solvent and the resulting filtrate was dissolved in tetrahydrofuran. The solution was filtered and to the filtrate was added a solution of hydrogen chloride in ether. The resulting precipitate was collected and recrystallized from hot water to yield 4.6 g. of N,N'-bis-[4-(4'-aminophenoxy)benzyl]-1,8-octanediamine in the form of its tetrahydrochloride, m.p. >300°C. (corr.).

Anal. Calcd. for $C_{34}H_{42}N_4O_2 \cdot 4HCl$: C, 59.64; H, 6.77; Cl, 20.72. Found: C, 59.49; H, 6.46; Cl, 20.71.

N,N'-bis[4-(4'-aminophenoxy)benzyl]-1,8-octanediamine when tested according to standard in vitro bacteriological procedures was found to have antibacterial activity, for example, as follows:

|  | Minimum Effective Concentration (mg./cc.) | |
| --- | --- | --- |
|  | Bacteriostatic | Bactericidal |
| *Staphylococcus aureus* | 0.0075 | 0.025 |
| *Eberthella typhi* | 0.05 | 0.075 |
| *Clostridium welchii* | 0.1 | 0.1 |
| *Pseudomonas aeruginosa* | 0.75 | 1.0 |
| *Streptococcus sp.* | 0.025 | 0.05 |

Following the procedure described in Example 14A using corresponding molar equivalent quantities of N,N'-bis-[4-(4'-nitrophenoxy)benzyl]-diamine, the following compounds can be prepared:

B. N,N'-bis[4-(4'-aminophenoxy)benzyl]-1,6-hexanediamine, using N,N'-bis[4-(4'-nitrophenoxy)benzyl]-1,6-hexanediamine.

C. N,N'-bis[4-(4'-aminophenoxy)benzyl]-N,N'-dimethyl-1,6-hexanediamine, using N,N'-bis[4-(4'-nitrophenoxy)benzyl]-N,N'-dimethyl-1,6-hexanediamine.

D. N,N'-bis[4-(4'-aminophenoxy)benzyl]-N,N'-diethyl-1,8-octanediamine, using N,N'-bis[4-(4'-nitrophenoxy)benzyl]-N,N'-diethyl-1,8-octanediamine.

E. N,N'-bis[4-(4'-aminophenoxy)benzyl]-N,N'-di-n-butyl-1,6-hexanediamine, using N,N'-bis[4-(4'-nitrophenoxy)benzyl]-N,N'-di-n-butyl-1,6-hexanediamine.

F. N,N'-bis[4-(4'-aminophenoxy)benzyl]-N,N'-di-n-hexyl-1,4-butanediamine, using N,N'-bis[4-(4'-nitrophenoxy)benzyl]-N,N'-di-n-hexyl-1,4-butanediamine.

G. N,N'-bis[4-(4'-aminophenoxy)benzyl]-N,N'-bis(phenylcarbamyl)-1,6-hexanediamine, using N,N'-bis[4-(4'-nitrophenoxy)benzyl]-N,N'-bis(phenylcarbamyl)-1,6-hexanediamine.

H. Trans-1,4-bis[4-(4'-aminophenoxy)benzylaminomethyl]cyclohexane, using trans-1,4-bis[4-(4'-nitrophenoxy)benzylaminomethyl]cyclohexane.

EXAMPLE 15

A. 1,4-Bis{2-[4-(4'-nitrophenoxy)benzalamino]ethyl}-2,3,5,6-tetramethylbenzene was prepared following the procedure described in Example 1 using 24.3 g. of 4-(4'-nitrophenoxy)benzaldehyde, 11.0 g. of 1,4-bis(2-aminoethyl)-2,3,5,6-tetramethylbenzene, 100 ml. of benzene and a reflux period of 5 hours. There was thus obtained 33 g. of the product, m.p. 168°–170°C.

B. 1,4-Bis[4-(4'-nitrophenoxy)benzalaminomethyl]-benzene can be prepared as in Example 15A using corresponding molar equivalent quantities of 4-(4'-nitrophenoxy)-benzaldehyde and 1,4-bis(aminomethyl)benzene.

C. 1,4-Bis{2-[4-(4'-nitrophenoxy)benzalamino]ethyl}-benzene can be prepared as in Example 15A using corresponding molar equivalent quantities of 4-(4'-nitrophenoxy)benzaldehyde and 1,4-bis(2-aminoethyl)benzene.

EXAMPLE 16

A. Bis{2-[4-(4'-nitrophenoxy)benzylamino]ethyl}-2,3,5,6-tetramethylbenzene — To a suspension containing 33 g. of 1,4-bis{2-[4-(4'-nitrophenoxy)benzalamino]ethyl}-2,3,5,6-tetramethylbenzene in a mixture of 600 ml. of methanol and 400 ml. of dioxane was added with stirring 5.7 g. of sodium borohydride. The resulting mixture was stirred for two hours, allowed to stand over the weekend at room temperature and then concentrated in vacuo to yield a semisolid material which was washed with water and made basic with 35 percent aqueous sodium hydroxide solution. The alkaline solution was extracted with tetrahydrofuran and the extract concentrated to a volume of about 100 ml. To the concentrate was added 10 ml. of concentrated hydrochloric acid. The solid that separated was boiled with methanol, collected and dried to yield 31.7 g. of bis{2-[4-(4'-nitrophenoxy)-benzylamino]ethyl}-2,3,5,6-tetramethylbenzene as its dihydrochloride, m.p. 262.2°–268.6°C. (corr.) with decomposition.

Anal. Calcd. for $C_{40}H_{42}N_4O_6 \cdot 2HCl$: Cl, 9.48; N, 7.49. Found: Cl, 9.71; N, 7.61.

Bis{2-[4-(4'-nitrophenoxy)benzylamino]ethyl}-2,3,5,6-tetramethylbenzene dihydrochloride when tested according to standard in vitro bacteriological procedures was found to have antibacterial activity, for example, as follows:

|  | Minimum Effective Concentration (mg./cc.) | |
| --- | --- | --- |
|  | Bacteriostatic | Bactericidal |
| *Staphylococcus aureus* | 0.0075 | 0.075 |
| *Eberthella typhi* | 0.1 | 0.75 |
| *Clostridium welchii* | 0.1 | 0.25 |
| *Streptococcus sp.* | 0.0025 | 0.025 |

Following the procedure described in Example 16A using corresponding molar equivalent quantities of the appropriate 1,4-bis[4(4'-nitrophenoxy)benzalaminoalkyl]-benzene and sodium borohydride, the following compounds can be prepared:

B. 1,4-Bis[4-(4'-nitrophenoxy)benzylaminomethyl]-benzene, using 1,4-bis[4-(4'-nitrophenoxy)benzylaminomethyl]-benzene.

C. 1,4-Bis{2-[4-(4'-nitrophenoxy)benzylamino]ethyl}-benzene, using 1,4-bis{2-[4-(4'-nitrophenoxy)-benzylamino]ethyl}-benzene.

EXAMPLE 17

Following the procedure described in Example 1A using molar equivalent quantities of 4-(4'-nitrophenoxy)-benzaldehyde and the appropriate diamine, the following compounds can be prepared:

A. 1,2-Bis[4-(4'-nitrophenoxy)benzalaminomethyl]-cyclopropane, using 1,2-bis(aminomethyl)cyclopropane.

B. 1,3-Bis[4(4'-nitrophenoxy)benzalaminomethyl]-cyclopentane, using 1,3-bis(aminomethyl)cyclopentane.

C. 2,6-Bis[4-(4'-nitrophenoxy)benzalaminomethyl]-pyridine, using 2,6-bis(aminomethyl)pyridine.

D. 2,5-Bis[4-(4'-nitrophenoxy)benzalaminomethyl]-pyridine, using 2,5-bis(aminomethyl)pyridine.

E. 3,4-Bis[4-(4'-nitrophenoxy)benzalaminomethyl]-pyridine, using 3,4-bis(aminomethyl)pyridine.

F. 2,5-Bis[4-(4'-nitrophenoxy)benzalaminomethyl]furan, using 2,5-bis(aminomethyl)furan.

G. 1,4-Bis[4(4'-nitrophenoxy)benzalaminomethyl]-2,5-dimethylbenzene, using 1,4-bis(aminomethyl)-2,5-dimethylbenzene.

H. 1,3-Bis[4-(4'-nitrophenoxy)benzalaminomethyl]-benzene, using 1,3-bis(aminomethyl)benzene.

I. 2,4-Bis{2-[4-(4'-nitrophenoxy)benzalamino]ethyl}thiazole, using 2,4-bis(2-aminoethyl)thiazole.

J. N,N'-bis[4-(4'-nitrophenoxy)benzal]-2-(2-aminomethylphenyl)ethylamine, using 2-(2-aminomethylphenyl)-ethylamine.

EXAMPLE 18

Following the procedure described in Example 6A using molar equivalent quantities of the appropriate bis[4-(4'-nitrophenoxy)benzal]-diamine and sodium borohydride, the following compounds can be prepared:

A. 1,2-Bis[4-(4'-nitrophenoxy)benzylaminomethyl]-cyclopropane, using 1,2-bis[4-(4'-nitrophenoxy)benzylaminomethyl]-cyclopropane.

B. 1,3-Bis[4-(4'-nitrophenoxy)benzylaminomethyl]-cyclopentane, using 1,3-bis[4-(4'-nitrophenoxy)benzylaminomethyl]cyclopentane.

C. 2,6-Bis[4-(4'-nitrophenoxy)benzylaminomethyl]-pyridine, using 2,6-Bis[4-(4'-nitrophenoxy)benzalaminomethyl]-pyridine.

D. 2,5-Bis[4-(4'-nitrophenoxy)benzylaminomethyl]-pyridine, using 2,5-Bis[4-(4'-nitrophenoxy)benzalaminomethyl]-pyridine.

E. 3,4-Bis[4-(4'-nitrophenoxy)benzylaminomethyl]-pyridine, using 3,4-Bis[4-(4'-nitrophenoxy)benzalaminomethyl]-pyridine.

F. 2,5-Bis[4-(4'-nitrophenoxy)benzylaminomethyl]-furan, using 2,5-Bis[4-(4'-nitrophenoxy)benzalaminomethyl]-furan.

G. 1,4-Bis[4-(4'-nitrophenoxy)benzylaminomethyl]-2,5-dimethylbenzene, using 1,4-bis[4-(4'-nitrophenoxy)benzalaminomethyl]-2,5-dimethylbenzene.

H. 1,3-Bis[4-(4'-nitrophenoxy)benzylaminomethyl]-benzene, using 1,3-Bis[4-(4'-nitrophenoxy)benzalaminomethyl]-benzene.

I. 2,4-Bis{2-[4-(4'-nitrophenoxy)benzylamino]ethyl}-thiazole, using 2,4-bis{2-[4-(4'-nitrophenoxy)benzalamino]ethyl}thiazole.

J. N,N'-bis[4-(4'-nitrophenoxy)benzyl]-2-(2-aminomethylphenyl)ethylamine, using N,N'-bis[4-(4'-nitrophenoxy)benzal]-2-(2-aminomethylphenyl)ethylamine.

EXAMPLE 19

Following the procedure described in Example 14A using corresponding molar equivalent quantities of the appropriate bis[4-(4'-nitrophenoxy)benzyl]-diamine, sodium borohydride and palladium-on-charcoal, the following corresponding bis[4-(4'-aminophenoxy)benzyl]-diamines can be prepared.

A. 1,2-Bis[4-(4'-aminophenoxy)benzylaminomethyl]-cyclopropane.

B. 1,3-Bis[4-(4'-aminophenoxy)benzylaminomethyl]-cyclopentane.

C. 2,6-Bis[4-(4'-aminophenoxy)benzylaminomethyl]-pyridine.

D. 2,5-Bis[4-(4'-aminophenoxy)benzylaminomethyl]-pyridine.

E. 3,4-Bis[4-(4'-aminophenoxy)benzylaminomethyl]-pyridine.

F. 2,5-Bis[4-(4'-aminophenoxy)benzylaminomethyl]-furan.

G. 1,4-Bis[4-(4'-aminophenoxy)benzylaminomethyl]-2,5-dimethylbenzene.

H. 1,3-Bis[4-(4'-aminophenoxy)benzylaminomethyl]-benzene.

I. 2,4-Bis{2-[4-(4'-aminophenoxy)benzylamino]ethyl}-thiazole.

J. N,N'-bis[4-(4'-aminophenoxy)benzyl]-2-(2-aminomethylphenyl)ethylamine.

EXAMPLE 20

Following the procedure described in Example 11A using molar equivalent quantities of the appropriate N,N'-bis[4-(4'-nitrophenoxy)benzyl]-diamine, formic acid and formaldehyde, the following corresponding N,N'-dimethyl compounds can be prepared:

A. N,N'-dimethyl-N,N'-bis[4-(4'-nitrophenoxy)-benzyl]-1,3-bis(aminomethyl)cyclopentane.

B. N,N'-dimethyl-N,N'-bis[4-(4'-nitrophenoxy)-benzyl]-1,2-bis(aminomethyl)cyclopropane.

C. N,N'-dimethyl-N,N'-bis[4-(4'-nitrophenoxy)-benzyl]-2,6-bis(aminomethyl)pyridine.

D. N,N'-dimethyl-N,N'-bis[4-(4'-nitrophenoxy)-benzyl]-2,5-bis(aminomethyl)pyridine.

E. N,N'-dimethyl-N,N'-bis[4-(4'-nitrophenoxy)-benzyl]-3,4-bis(aminomethyl)pyridine.

F. N,N'-dimethyl-N,N'-bis[4-(4'-nitrophenoxy)-benzyl]-2,5-bis(aminomethyl)furan.

G. 2,5,N,N'-tetramethyl-N,N'-bis[4-(4'-nitrophenoxy)-benzyl]-1,4-bis(aminomethyl)benzene.

H. N,N'-dimethyl-N,N'-bis[4-(4'-nitrophenoxy)benzyl]-1,3-bis(aminomethyl)benzene.

I. N,N'-dimethyl-N,N'-bis[4-(4'-nitrophenoxy)benzyl]-2,4-bis(aminoethyl)thiazole.

J. N,N'-dimethyl-N,N'-bis[4-(4'-nitrophenoxy)benzyl]-2-(2-aminomethylphenyl)ethylamine.

EXAMPLE 21

Following the procedure described in Example 12A using molar equivalent quantities of the appropriate N,N'-bis[(4-(4'-nitrophenoxy)benzyl]-diamine and phenyl isocyanate, the following corresponding N,N'-bis(phenylcarbamyl) compounds can be prepared:

A. N,N'-bis[4-(4'-nitrophenoxy)benzyl]-N,N'-bis-(phenylcarbamyl)-1,2-bis(aminomethyl)cyclopropane.

B. N,N'-bis[4-(4'-nitrophenoxy)benzyl]-N,N'-bis-(phenylcarbamyl)-1,3-bis(aminomethyl)cyclopentane.

C. N,N'-bis[4-(4'-nitrophenoxy)benzyl]-N,N'-bis-(phenylcarbamyl)-2,6-bis(aminomethyl)pyridine.

D. N,N'-bis[4(4'-nitrophenoxy)benzyl]-N,N'-bis-(phenylcarbamyl)-2,5-bis(aminomethyl)pyridine.

E. N,N'-bis[4-(4'-nitrophenoxy)benzyl]-N,N'-bis-(phenylcarbamyl)-3,4-bis(aminomethyl)pyridine.

F. N,N'-bis[4-(4'-nitrophenoxy)benzyl]-N,N'-bis-(phenylcarbamyl)-2,5-bis(aminomethyl)furan.

G. N,N'-bis[4-(4'-nitrophenoxy)benzyl]-N,N'-bis-(phenylcarbamyl)-1,4-bis(aminomethyl)-2,5-dimethylbenzene.

H. N,N'-bis[4(4'-nitrophenoxy)benzyl]-N,N'-bis-(phenylcarbamyl)-1,3-bis(aminomethyl)benzene.

I. N,N'-bis[4-(4'-nitrophenoxy)benzyl]-N,N'-bis(phenylcarbamyl)-2,4-bis(2-aminoethyl)thiazole.

J. N,N'-bis[4(4'-nitrophenoxy)benzyl]-N,N'-bis(phenylcarbamyl)-2-(2-aminomethylphenyl)ethylamine.

EXAMPLE 22

Following the procedure described in Example 13A using corresponding molar equivalent quantities of the appropriate N,N'-bis[4-(4'-nitrophenoxy)benzyl]-diamine and dichloroacetyl chloride, the following corresponding N,N'-bis(dichloroacetyl) compounds can be prepared:

A. N,N'-bis(dichloroacetyl)-N,N'-bis[4-(4'-nitrophenoxy)benzyl]-1,2-bis(aminomethyl)cyclopropane.

B. N,N'-bis(dichloroacetyl)-N,N'-bis[4-(4'-nitrophenoxy)benzyl]-1,3-bis(aminomethyl)cyclopentane.

C. N,N'-bis(dichloroacetyl)-N,N'-bis[4-(4'-nitrophenoxy)benzyl]-2,6-bis(aminomethyl)pyridine.

D. N,N'-bis(dichloroacetyl)-N,N'-bis[4-4'-nitrophenoxy)benzyl]-2,5-bis(aminomethyl)pyridine.

E. N,N'-bis(dichloroacetyl)-N,N'-bis[4-(4'-nitrophenoxy)benzyl]-3,4-bis(aminomethyl)pyridine.

F. N,N'-bis(dichloroacetyl)-N,N'-bis[4-(4'-nitrophenoxy)benzyl]-2,5-bis(aminomethyl)furan.

G. N,N'-bis(dichloroacetyl)-N,N'-bis[4-(4'-nitrophenoxy)benzyl]-1,4-bis(aminomethyl)-2,5-dimethylbenzene.

H. N,N'-bis(dichloroacetyl)-N,N'-bis[4-(4'-nitrophenoxy)benzyl]-1,3-bis(aminomethyl)benzene.

I. N,N'-bis(dichloroacetyl)-N,N'-bis[4-(4'-nitrophenoxy)benzyl]-2,4-bis(2-aminoethyl)thiazole.

J. N,N'-bis(dichloroacetyl)-N,N'-bis[4-(4'-nitrophenoxy)benzyl]-2-(2-aminomethylphenyl)ethylamine.

I claim:

1. A compound of the formula

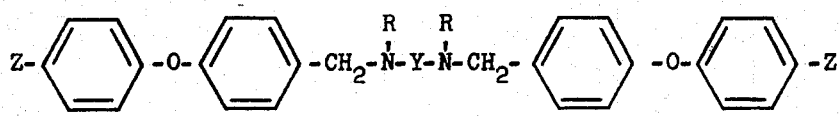

wherein Z is nitro or amino; R is phenylcarbamyl or dihaloacetyl; and Y is alkylene having from two to ten carbon atoms and having its connecting linkages on different carbon atoms or said alkylene interrupted by O, S, NH, N(lower-alkyl), cycloalkylene having from three to six ring carbon atoms, phenylene or phenylene having from one to four lower-alkyl substituents.

2. A compound according to claim 1, wherein Z is nitro or amino; R is phenylcarbamyl; and Y is alkylene having from two to ten carbon atoms and having its connecting linkages on different carbon atoms or said alkylene interrupted by O, S, NH, N(lower-alkyl), cycloalkylene having from three to six ring carbon atoms, phenylene, phenylene having from one to four lower-alkyl substituents.

3. N,N'-bis[4-(4'-nitrophenoxy)benzyl]-N,N'-bis(phenylcarbamyl)-1,6-hexanediamine according to claim 2.

4. A compound according to claim 1, wherein Z is nitro or amino; R is dihaloacetyl; and Y is alkylene having from two to 10 carbon atoms and having its connecting linkages on different carbon atoms or said alkylene interrupted by O, S, NH, N(lower-alkyl), cycloalkylene having from three to six ring carbon atoms, phenylene, phenylene having from one to four lower-alkyl substituents.

5. N,N'-bis(dichloroacetyl)-N,N'-bis[4-(4'-nitrophenoxy)benzyl]-1,2-ethanediamine according to claim 4.

* * * * *